US00PP20871P2

(12) United States Plant Patent
Murakami

(10) Patent No.: US PP20,871 P2
(45) Date of Patent: Mar. 23, 2010

(54) *NIEREMBERGIA* PLANT NAMED 'SUNNICOPAHO'

(50) Latin Name: *Nierembergia hybrida*
Varietal Denomination: Sunnicopaho

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/284,881

(22) Filed: Sep. 22, 2008

(51) Int. Cl.
*A01H 5/00* (2006.01)

(52) U.S. Cl. ..... Plt./459

(58) Field of Classification Search ..... Plt./459
See application file for complete search history.

(56) References Cited

U.S. PATENT DOCUMENTS

PP19,103 P2 * 8/2008 Murakami ..... Plt./459

OTHER PUBLICATIONS

UPOV ROM GTITM Computer Database, GTI Jouve Retrieval Software 2009/03 Citation for 'Sunnicopaho'.*

* cited by examiner

*Primary Examiner*—Wendy C Haas
(74) *Attorney, Agent, or Firm*—C. A. Whealy

(57) ABSTRACT

A new and distinct cultivar of *Nierembergia* plant named 'Sunnicopaho', characterized by its compact, upright and mounding plant habit; freely branching habit; freely, continuous and early flowering habit; large white-colored flowers; and long flowering period.

1 Drawing Sheet

Botanical designation: *Nierembergia hybrida.*
Cultivar denomnation: 'Sunnicopaho'.

BACKGROUND OF THE INVENTION

The present invention relates to a new and distinct cultivar of *Nierembergia*, botanically known as *Nierembergia hybrida* and hereinafter referred to by the name 'Sunnicopaho'.

The new *Nierembergia* plant is a product of a planned breeding program conducted by the Inventor in Higashiomi, Shiga, Japan. The objective of the breeding program was to create new compact mounding *Nierembergia* cultivars with freely branching habit, early flowering habit and attractive flower coloration.

The new *Nierembergia* plant originated from a cross-pollination made by the Inventor in 2003, in Higashiomi, Shiga, Japan, of a proprietary selection of *Nierembergia hybrida* identified as code number NB13, not patented, as the female, or seed, parent with a proprietary selection of *Nierembergia hybrida* identified as code number NS1, not patented, as the male, or pollen, parent. The new *Nierembergia* was discovered and selected by the Inventor as a single flowering plant within the progeny of the stated cross-pollination in a controlled environment in Higashiomi, Shiga, Japan in October, 2004.

Asexual reproduction of the new *Nierembergia* plant by vegetative cuttings in a controlled environment in Higashiomi, Shiga, Japan since December, 2004, has shown that the unique features of this new *Nierembergia* plant are stable and reproduced true to type in successive generations.

SUMMARY OF THE INVENTION

Plants of the new *Nierembergia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunnicopaho'. These characteristics in combination distinguish 'Sunnicopaho' as a new and distinct cultivar of *Nierembergia:*

1. Compact, upright and mounding plant habit.
2. Freely branching habit.
3. Freely, continuous and early flowering habit.
4. Large white-colored flowers.
5. Long flowering period.
6. Good garden performance.

Plants of the new *Nierembergia* differ from plants of the female parent selection in the following characteristics:

1. Plants of the new *Nierembergia* are more compact than plants of the female parent selection.
2. Plants of the new *Nierembergia* flower earlier than plants of the female parent selection.
3. Plants of the new *Nierembergia* and the female parent selection differ in flower color as plants of the female parent selection have blue-colored flowers.

Plants of the new *Nierembergia* differ from plants of the male parent selection in the following characteristics:

1. Plants of the new *Nierembergia* are more freely branching than plants of the male parent selection.
2. Plants of the new *Nierembergia* have thinner stems than plants of the male parent selection.
3. Plants of the new *Nierembergia* flower earlier than plants of the male parent selection.

Plants of the new *Nierembergia* can be compared to plants of *Nemesia hybrida* 'Sunnipariho', disclosed in U.S. Plant Pat. No. 19,103. In side-by-side comparisons conducted in Higashiomi, Shiga, Japan, plants of the new *Nierembergia* and 'Sunnipariho' differed in the following characteristics:

1. Plants of the new *Nierembergia* were shorter than and not as broad as plants of 'Sunnipariho'.

2. Plants of the new *Nierembergia* were not as upright as plants of 'Sunnipariho'.
3. Plants of the new *Nierembergia* were more freely branching than plants of 'Sunnipariho'.
4. Plants of the new *Nierembergia* had thicker stems than plants of 'Sunnipariho'.
5. Plants of the new *Nierembergia* had smaller leaves than plants of 'Sunnipariho'.
6. Plants of the new *Nierembergia* flowered earlier than plants of 'Sunnipariho'.
7. Plants of the new *Nierembergia* had smaller flowers than plants of 'Sunnipariho'.

BRIEF DESCRIPTION OF THE PHOTOGRAPHS

The accompanying colored photographs illustrate the overall appearance of the new *Nierembergia*, showing the colors as true as it is reasonably possible to obtain in colored reproductions of this type. Colors in the photographs may differ slightly from the color values cited in the detailed botanical description which accurately describe the colors of the new *Nierembergia*.

The photograph at the top of the sheet comprises a side perspective view of a typical flowering plant of 'Sunnicopaho' grown in a container.

The photograph at the bottom of the sheet is a close-up view of typical flowers, flower buds and leaves of 'Sunnicopaho'.

DETAILED BOTANICAL DESCRIPTION

The aforementioned photographs and following observations, measurements and values describe plants grown in Higashiomi, Sihiga, Japan, under commercial practice during the spring and early summer in an outdoor nursery with day temperatures averaging 23° C. and night temperatures averaging 13° C. After planting, plants had been growing for seven months when the photographs and description were taken. In the following description, color references are made to The Royal Horticultural Society Colour Chart, 2001 Edition, except where general terms of ordinary dictionary significance are used.

Botanical classification: *Nierembergia hybrida* 'Sunnicopaho'.

Parentage:

*Female, or seed, parent.*—Proprietary selection of *Nierembergia hybrida* identified as code number NB13, not patented.

*Male, or pollen, parent.*—Proprietary selection of *Nierembergia hybrida* identified as code number NS1, not patented.

Propagation:

*Type.*—By vegetative cuttings.

*Time to initiate roots.*—About two weeks at 20° C. to 25° C.

*Time to produce a rooted young plant roots.*—About five weeks at 20° C. to 25° C.

*Root description.*—Fibrous; white in color.

*Rooting habit.*—Freely branching; moderately dense.

Plant description:

*Plant form/habit.*—Compact and mounded plant habit; outwardly spreading; vigorous growth habit. Freely branching habit; pinching enhances branching potential.

*Plant height.*—About 14.6 cm.

*Plant width (spread).*—About 32.4 cm.

*Lateral branches.*—Length: About 20.9 cm. Diameter: About 1.6 mm. Internode length: About 5 mm. Strength: Strong. Texture: Pubescent. Color: Close to 144A.

Foliage description:

*Arrangement.*—Alternate, simple; sessile.

*Length.*—About 2.5 cm.

*Width.*—About 4 mm.

*Shape.*—Lanceolate.

*Apex.*—Acute.

*Base.*—Truncate.

Margin.—Entire.

*Texture, upper and lower surfaces.*—Pubescent.

*Venation pattern.*—Pinnate.

*Color.*—Developing and fully developed leaves, upper surface: Close to 137B; venation, close to 137B. Developing and fully developed leaves, lower surface: Close to 137C; venation, close to 137C.

Flower description:

*Flower type/habit.*—Single salverform flowers; flowers face mostly upright. Freely flowering habit with about 29 flowers developing per plant. Early flowering habit, plants begin flowering about 4.5 weeks after planting rooted young plants.

*Fragrance.*—None detected.

*Natural flowering season.*—Long and continuous flowering habit from spring to late autumn in Higashiomi, Shiga, Japan.

*Postproduction longevity.*—Flowers last about five days on the plant; flowers not persistent.

*Flower buds.*—Height: About 2.2 cm. Diameter: About 4.7 mm. Shape: Clavate. Color: Close to 155A.

*Flower diameter.*—About 3.3 cm.

*Flower depth.*—About 3 cm.

*Petals.*—Quantity per flower: Typically five in a single whorl; petals fused. Length: About 1.2 cm to 1.9 cm. Lobe width: About 1.6 cm. Tube length: About 1.6 cm. Tube diameter: About 1.1 mm. Shape: Roughly spatulate. Apex: Obtuse. Margin: Slightly crenate to entire; slightly undulate. Texture, upper and lower surfaces: Smooth, glabrous. Texture, tube: Pubescent. Color: Developing and fully developed petals, upper surface: Close to 155C; towards the center, 6A. Developing and fully developed petals, lower surface: Close to 155C. Throat: Close to 1 50D. Tube: Close to 150D.

*Sepals.*—Quantity per flower: Typically five in a single whorl, fused at base; star-shaped calyx. Length: About 4.1 mm. Width: About 2 mm. Shape: Lanceolate. Apex: Acute. Margin: Entire. Texture, upper and lower surfaces: Smooth, glabrous. Color, upper and lower surfaces: Close to 137C.

*Peduncles.*—Length: About 1.6 cm. Diameter: About 0.7 mm. Texture: Smooth, glabrous. Color: Close to 144B.

*Reproductive organs.*—Stamens: Quantity per flower: Typically five. Stamen length: About 6.3 mm. Anther shape: Globose. Anther size: About 1.9 mm by 1.4 mm. Anther color: Close to 6D. Pollen amount: Moderate. Pollen color: Close to 6B. Pistils: Quantity per flower: One. Pistil length: About 2.2 cm. Stigma shape: Globose. Stigma color: Close to 144B. Style color: Close to 145C. Ovary color: Close to 137C.

*Seed/fruit.*—Seed and fruit development have not been observed.

Disease/pest resistance: Plants of the new *Nierembergia* have not been noted to be resistant to pathogens and pests common to *Nierembergia*.

Garden performance: Plants of the new *Nierembergia* have been observed to have good garden performance and tolerate rain, wind and temperatures from about −5° C. to about 35° C.

It is claimed:

1. A new and distinct *Nierembergia* plant named 'Sunnicopaho' as illustrated and described.

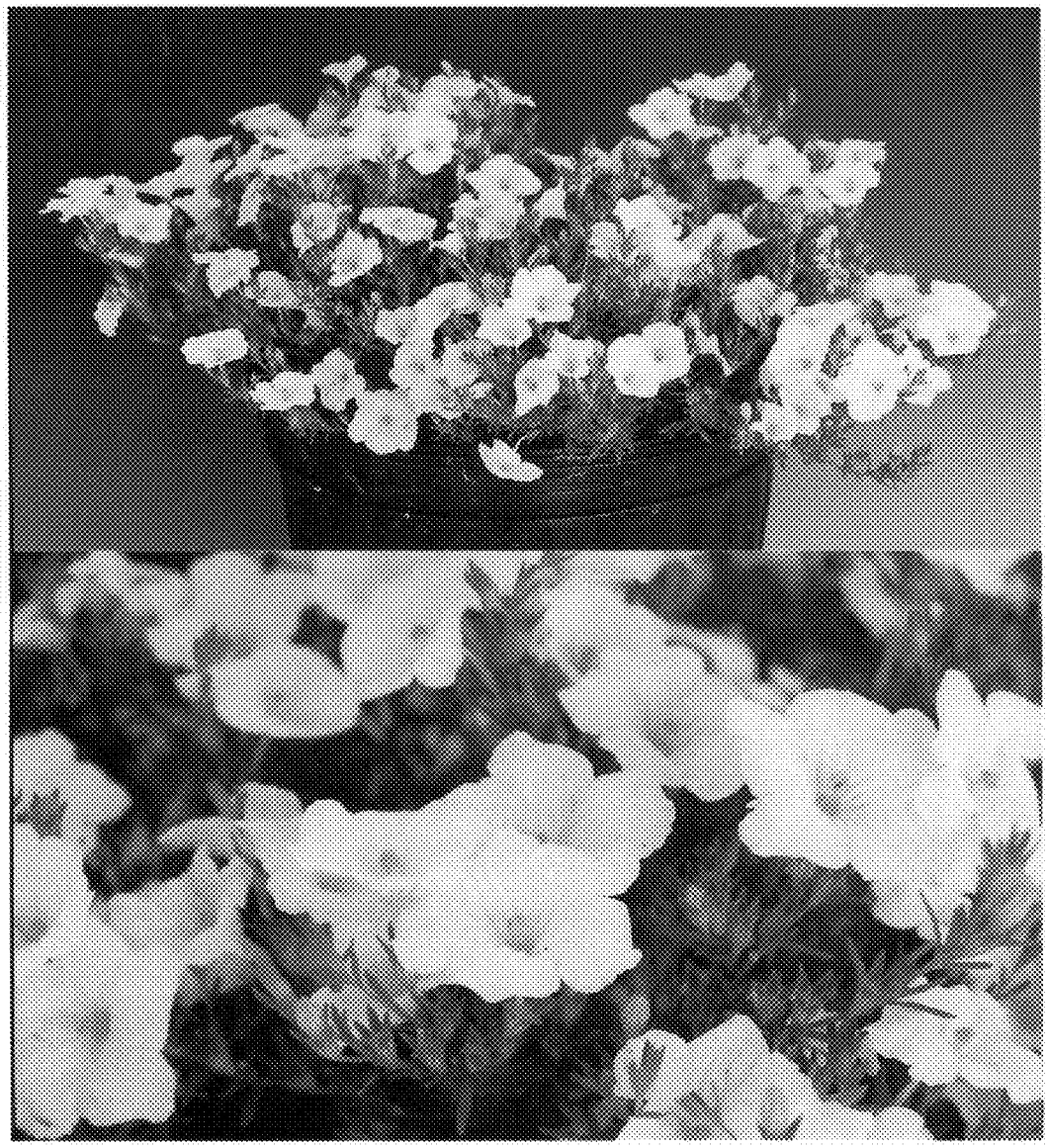

* * * * *